United States Patent
Ries et al.

(10) Patent No.: US 9,401,562 B2
(45) Date of Patent: Jul. 26, 2016

(54) DOWN THE BORE WITH OPEN WINDOWS AND MANUFACTURING THEREOF

(71) Applicant: Medtronic, Inc., Minneapolis, MN (US)

(72) Inventors: Andrew J Ries, Lino Lakes, MN (US); Jeffrey A Swanson, Cambridge, MN (US); George A Patras, Greenfield, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/695,036

(22) Filed: Apr. 23, 2015

(65) Prior Publication Data

US 2015/0306402 A1  Oct. 29, 2015

Related U.S. Application Data

(60) Provisional application No. 61/984,385, filed on Apr. 25, 2014, provisional application No. 61/984,367, filed on Apr. 25, 2014.

(51) Int. Cl.
| | |
|---|---|
| *A61N 1/00* | (2006.01) |
| *H01R 13/52* | (2006.01) |
| *A61N 1/375* | (2006.01) |
| *H01R 24/58* | (2011.01) |
| *A61N 1/05* | (2006.01) |
| *B29C 45/14* | (2006.01) |
| *H01R 13/66* | (2006.01) |
| *H01R 107/00* | (2006.01) |
| *B29L 31/00* | (2006.01) |

(52) U.S. Cl.
CPC .......... *H01R 13/5202* (2013.01); *A61N 1/0587* (2013.01); *A61N 1/3752* (2013.01); *A61N 1/3754* (2013.01); *B29C 45/14639* (2013.01); *H01R 13/665* (2013.01); *H01R 24/58* (2013.01); *B29L 2031/753* (2013.01); *H01R 2107/00* (2013.01); *H01R 2201/12* (2013.01)

(58) Field of Classification Search
CPC . A61N 1/3754; A61N 1/0587; A61N 1/3752; H01R 13/5219; H01R 2107/00; H01R 24/58; H01R 43/24; H01R 13/5202; H01R 13/665; H01R 2201/12; B29C 45/14639; B29L 2031/753

See application file for complete search history.

(56) References Cited

U.S. PATENT DOCUMENTS

| | | | |
|---|---|---|---|
| 6,799,072 | B2 | 9/2004 | Ries et al. |
| 6,817,905 | B2 | 11/2004 | Zart et al. |

(Continued)

FOREIGN PATENT DOCUMENTS

| | | |
|---|---|---|
| WO | 03075414 A1 | 9/2003 |
| WO | 2009045772 A1 | 4/2009 |

OTHER PUBLICATIONS (PCT/US2015/027664) PCT Notification of Transmittal of the International Search Report and the Written Opinion of the International Searching Authority.

*Primary Examiner* — George Manuel
(74) *Attorney, Agent, or Firm* — Carol F. Barry

(57) ABSTRACT

An implantable medical device connector assembly and method of manufacture include a molded, insulative shell having an inner surface forming a connector bore, a circuit member including one or more traces extending through apertures in the connector shell. One or more conductive members, positioned along the connector bore, are electrically coupled to the traces. The sealing members are positioned between the conductive members.

9 Claims, 15 Drawing Sheets

(56) References Cited

U.S. PATENT DOCUMENTS

| | | |
|---|---|---|
| 6,895,276 B2 | 5/2005 | Kast et al. |
| 7,155,283 B2 | 12/2006 | Ries et al. |
| 7,164,951 B2 | 1/2007 | Ries et al. |
| 7,231,253 B2 | 6/2007 | Tidemand et al. |
| 7,309,262 B2 | 12/2007 | Zart et al. |
| 7,317,946 B2 | 1/2008 | Twetan et al. |
| 7,413,482 B2 * | 8/2008 | Ries et al. .............. 439/736 |
| 7,526,339 B2 | 4/2009 | Lahti et al. |
| 7,717,754 B2 | 5/2010 | Ries et al. |
| 7,988,497 B2 | 8/2011 | Ries et al. |
| 8,032,221 B2 | 10/2011 | Wengreen et al. |
| 8,062,074 B2 | 11/2011 | Ries et al. |
| 8,065,007 B2 | 11/2011 | Ries et al. |
| 8,123,567 B2 | 2/2012 | Kast et al. |
| 8,190,260 B2 | 5/2012 | Ries et al. |
| 8,206,180 B1 | 6/2012 | Kast et al. |
| 8,401,649 B2 | 3/2013 | Tronnes et al. |
| 8,412,330 B2 | 4/2013 | Kast et al. |
| 8,473,056 B2 | 6/2013 | Engmark et al. |
| 8,628,348 B2 | 1/2014 | Ries et al. |
| 8,700,160 B2 | 4/2014 | Troosters et al. |
| 8,706,229 B2 | 4/2014 | Lahti et al. |
| 8,792,984 B2 | 7/2014 | Kast et al. |
| 8,945,451 B2 | 2/2015 | Ries et al. |
| 2005/0137642 A1 | 6/2005 | Zart et al. |
| 2007/0100386 A1 | 5/2007 | Tronnes et al. |
| 2009/0017700 A1 | 1/2009 | Zart et al. |
| 2009/0266573 A1 | 10/2009 | Engmark et al. |
| 2010/0197174 A1 | 8/2010 | Lahti et al. |
| 2010/0285697 A1 | 11/2010 | Zart et al. |
| 2011/0014807 A1 | 1/2011 | Ries et al. |
| 2011/0190833 A1 | 8/2011 | Ries et al. |
| 2012/0149254 A1 | 6/2012 | Kast et al. |
| 2012/0215296 A1 | 8/2012 | Ries et al. |
| 2013/0218223 A1 | 8/2013 | Ghosh et al. |
| 2013/0226266 A1 | 8/2013 | Murtonen et al. |
| 2013/0307184 A1 | 11/2013 | Ries et al. |
| 2013/0309889 A1 | 11/2013 | Ries et al. |
| 2014/0052225 A1 | 2/2014 | Kast et al. |
| 2014/0123490 A1 | 5/2014 | Ries et al. |

* cited by examiner

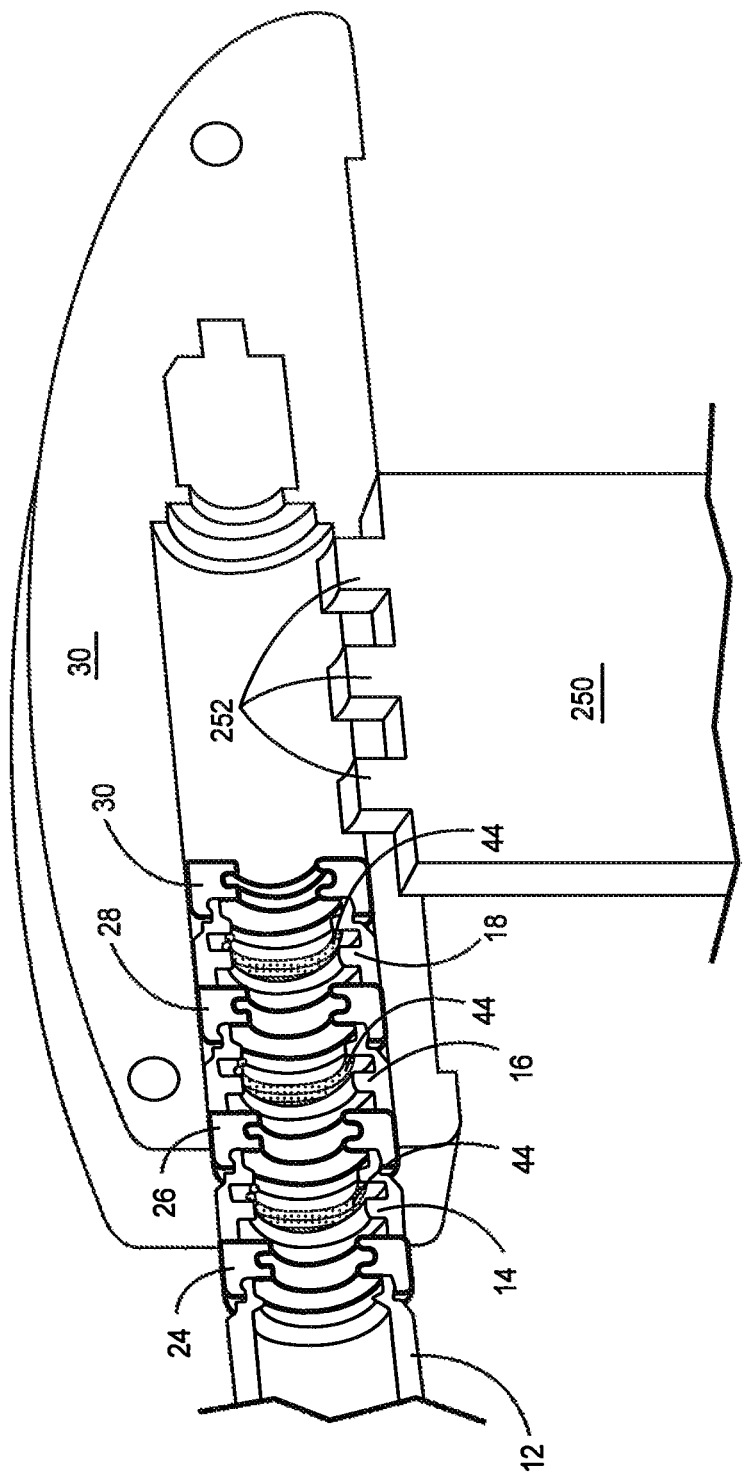

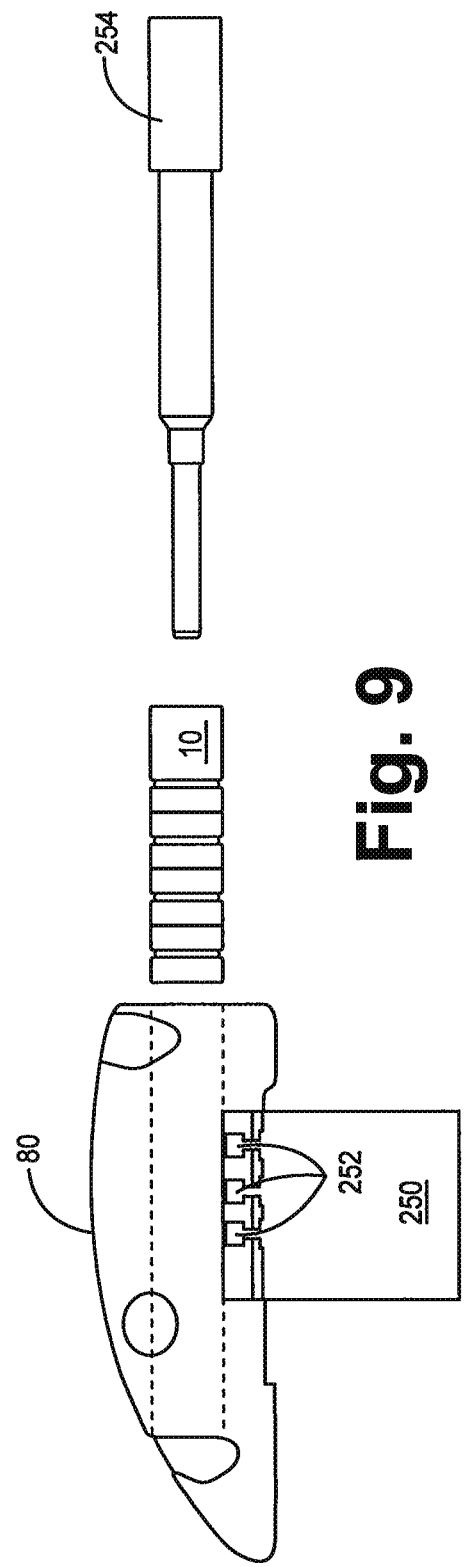

DOWN THE BORE WITH OPEN WINDOWS AND MANUFACTURING THEREOF

CROSS-REFERENCE TO RELATED APPLICATIONS

This application claims the benefit of U.S. Provisional Application No. 61/984,367, and 61/984,385 filed on Apr. 25, 2014. The disclosure of the above applications are incorporated herein by reference in their entirety.

This application is related to U.S. Pat. No. 9,362,660, filed on the same day entitled "DOWN THE BORE WITH OPEN WINDOWS AND MANUFACTURING THEREOF", herein incorporated by reference in its entirety.

TECHNICAL FIELD

The present disclosure relates generally to implantable medical device connector assemblies, and, more particularly, to a device connector that includes a connector shell with open windows thereby allowing a direct electrical connection between a stacked assembly and an implantable medical device hybrid circuit board.

BACKGROUND

Electrical connectors and other similar electrical components often include electrical conductors embedded within an insulating block to isolate the conductor from the surrounding environment. Embedding the conductor within a block protects the conductor and prevents the delivery of an unintended electrical shock. Electrical connector assemblies are coupled to a hermetically sealed housing of an implantable medical device that encloses internal circuitry such as a hybrid circuit board and one or more batteries. Such a medical device connector assembly is adapted for receiving medical leads used with the implantable medical device.

Methods for forming electrical connector assemblies having conductors embedded within an insulating block may include injection molding techniques or thermoset casting techniques. One method for forming an implantable medical device connector assembly with embedded conductors is generally disclosed in U.S. Pat. No. 6,817,905 (Zart et al.). The method generally includes forming a core portion using either an injection molding process or a machining process. The core portion is fitted with electrically conductive components and submitted to a subsequent overmold process in which a second shot of polymer material is injected into the mold. This process allows complex connector structures to be manufactured in a fast production cycle.

Another exemplary method is described in U.S. Pat. No. 8,628,348, which involves molding a connector shell with a set of closed conductive windows disposed down the bore of the connector shell. The closed conductive windows allows the inner surface of the cylindrical bore to be flush. A stacked subassembly, comprised of seals interleaved with conductive connectors, is then inserted and pushed down the bore while the stacked subassembly remains constrained within the cylindrical bore. Each seal is positioned between closed conductive windows while the conductive connectors are positioned over the conductive windows. A wire, extending from a feedthrough electronic assembly connected to a hybrid board, is then welded to each closed conductive window.

Numerous constructions and assembly methods for implantable medical device connector module assemblies are known in the art, some of which are disclosed in commonly assigned U.S. Pat. Nos. 6,895,276, 7,309,262, 7,317,946, 7,526,339, 7,717,754 and 8,032,221. However, there is still a need for new and improved connector module assembly constructions and associated assembly methods.

BRIEF DESCRIPTION OF THE DRAWINGS

FIGS. 8A-8B are schematic views of a mating tool used to fill apertures in a connector shell so that the inner surface down the bore of the connector shell is substantially flush.

FIG. 9 is a schematic view of a connector shell with a mating tool inserted into apertures with the stacked assembly in position to be inserted down the bore by an insertion tool.

SUMMARY

One or more embodiments of the disclosure involve a method for forming an implantable medical device including a connector assembly adapted to connect to a medical electrical lead. The method comprises providing a circuit member that includes electrical circuitry. A shell is molded using a polymer. The shell includes first and second opposing sides extending between first and second ends thereof. A bore is defined through at least one of the first and second ends of the shell to a bore distal end. A plurality of windows being defined through at least one of the first and second sides of the shell and disposed along the bore. A mating tool is moved adjacent to the plurality of windows. The mating tool comprises a head having a set of prongs. The set of prongs are positioned within the plurality of windows to close each window while forming a stacked subassembly within the bore. A stacked subassembly is formed along the connector bore. The stacked subassembly is formed by positioning a first pair of members comprising a first conductive member and a first sealing member along the connector bore. The first conductive member and the first sealing member are positioned together. The first conductive member has a surface exposed through a first window of the plurality of windows disposed in one of the first and second sides of the shell. A second pair of members are positioned together along the bore. The second pair comprises a second conductive member and a second sealing member. The second conductive member has a surface exposed through a second window of the plurality of windows disposed in one of the first and second sides of the shell. A plurality of conductive traces, extending along at least one of the first and second sides of the shell from the circuit member, are coupled to the first and second conductive members through the first and second windows.

DETAILED DESCRIPTION

In the following description, references are made to illustrative embodiments for carrying out the invention. It is understood that other embodiments may be utilized without departing from the scope of the invention. Unless otherwise indicated, drawing elements are not shown to scale.

Figure 1:
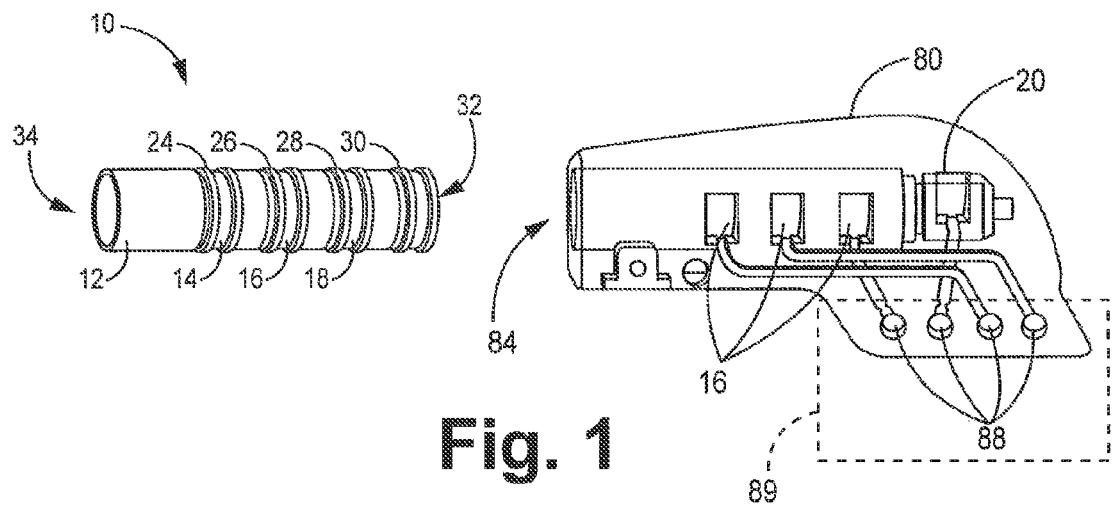
FIG. 1 illustrates a first embodiment perspective view of a stacked subassembly prior to being placed down a bore of a connector shell to form an implantable medical device connector.

The present disclosure is directed to an implantable medical device including a connector assembly adapted for receiving a medical electrical lead. A shell is molded that includes first and second ends with a bore extending therebetween. The shell further includes a plurality apertures or open windows along the bore. A mating tool is moved along the outer surface of the shell and adjacent to the plurality of apertures. The mating tool then contacts and fills the apertures. After the mating tool filled the apertures, the connector bore is flush or substantially flush which allows the stacked subassembly to be positioned in the connector bore. The stacked subassembly comprises a plurality of conductive members with sealing members interleaved between each conductive member (also referred to as contact) after insertion into the bore. Each conductive member is disposed within an aperture of the plurality of apertures formed in the shell to allow electrical connection through the aperture. Additionally, a plurality of sealing members are positioned between the conductive members and between the apertures where the bore diameter is continuous. The mating tool is moved away from the plurality of the apertures in response to the plurality of conductive members being positioned along the connector bore such that the set of conductive members are located within the plurality of apertures. A plurality of conductive traces extending from a circuit member (i.e. hybrid board) are coupled to the plurality of conductive members extending through a side of the shell. Simple single bore designs as shown in FIG. 1 and described herein achieve the highest cost effectiveness compared to other methods. For example, the disclosed method uses less interconnect welds since feedthough wires can be directly placed on conductive connectors members without using additional components or welded interfaces.

FIG. 1 is a perspective view of an exemplary stacked subassembly 10 which is inserted into shell 80 to form an implantable medical device connector assembly. Stacked subassembly 10 includes an end cap 12 and a set of conductive connectors 14, 16, and 18 (also referred to as ferrules or contacts) separated by sealing members 24, 26, 28 and 30. Shell 80, a first embodiment, has a feedthrough that exits from the side of the housing (also referred to as a "can") on a skirt 89 (also referred to as a flange). Connector 20 is adapted for receiving a lead pin terminal 52 and includes an open end aperture 32 through which a pin terminal of a lead connector assembly may be inserted. Connector 20 is shown embodied as a set screw block and further includes a set screw aperture 22 for receiving a set screw (not shown) used for securing the pin terminal of a lead connector assembly to retain the lead connector assembly within a connector bore formed by stacked subassembly 10. Connector 20 may alternatively be embodied as a spring contact or other contact adapted for receiving and engaging a lead pin terminal. The remainder of the connectors 14, 16, and 18 may be embodied as multi-beam contacts, spring contacts, or any other suitable electrical contacts for making electrical connection with lead connector terminals that become aligned with connectors 14, 16, and 18 when the lead connector assembly is fully inserted into stacked subassembly 10. End cap 12 is provided with an open receptacle 34 for receiving a lead connector assembly and acts to terminate the stack. End cap 12 is generally formed of a rigid material which may be conductive or non-conductive.

Sealing members 24, 26, and 28 are fabricated from an insulating material to electrically isolate connectors 14, 16, and 18. Sealing members 24, 26, and 28 are typically formed of a compliant material, such as a medical grade silicone rubber, such that sealing members 24, 26, and 28 form a fluid-resistant seal with insulating structures of a lead connector. When the lead connector is fully inserted into stacked subassembly 10, which has been assembled in an IMD connector assembly, sealing members 24, 26, and 28 are aligned with insulating structures separating lead connector terminals. An inner surface of sealing members 24, 26, and 28 will form a fluid-resistant interface with the insulating structures of the lead connector assembly, thereby preventing body fluids from creating a short circuit between lead terminals and stacked subassembly connectors 14, 16, 18, and 20.

Stacked subassembly 10 can either be pre-assembled or assembled in the bore 84 of the shell 80. Skilled artisans appreciate that the pairs of conductive connector members 14, 16, 18 and seals 24, 26, 28 may be two or more to form a stacked assembly 10. For example, in one or more embodiments, a first pair members, is inserted down the bore 84 such that a first seal member 28 enters the bore 84 first followed by the first conductive connector 18. The first pair of members are positioned at a distal end of the bore 84. The second pair of members, comprising a second seal member 26 enters the bore 84 followed by the second conductive connector 16. The second seal member 26 is adjacent first conductive connector 18. Optionally, a third pair is positioned down the bore 84 such that a third seal member 24 is inserted down the bore 84 followed by the conductive connector 14. The third seal member 24 is adjacent second conductive connector 16. After the first, second and third pairs of conductive connector and seals have been positioned down the bore 84, the end cap 12 is then inserted thereby completing the down the bore 84 assembly.

Stacked subassembly 10 can also be loaded onto an insertion tool and then inserted into the bore 84. An exemplary insertion tool is shown and described in U.S. Pat. No. 7,717,754 issued Jun. 12, 2008, and assigned to the assignee of the present invention, the disclosure of which is incorporated by reference in its entirety herein. The tip of the insertion tool is used to apply pressure along a surface of stacked subassembly 10 until the stacked subassembly 10 is fully inserted into connector bore 84. In one or more embodiments, it may be beneficial to insert each contact/seal pair individually to ensure accurate position of each contact within each aperture along the bore 84. An adhesive, such as an epoxy, a urethane, a silicone medical adhesive, or other suitable thermoset material, is injected through a fill port to form adhesive bonds between the outer surface of sealing members 24, 26, and 28 and shell inner surface 82. A two-part adhesive may be pre-mixed prior to injection. Examples of suitable adhesives include epoxy and urethane medical application adhesives available from Master Bond, Inc., Hackensack, N.J.

Figure 2:
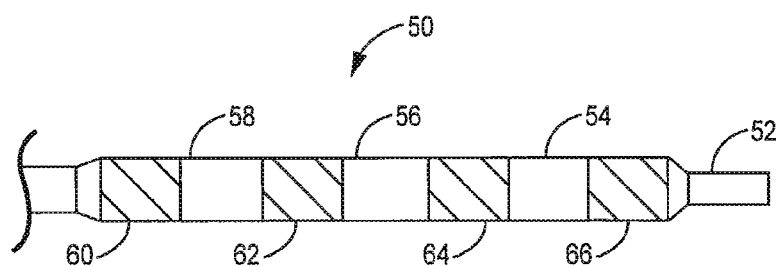
FIG. 2 is a plan view of a proximal lead connector assembly adapted for use with the stacked subassembly of FIG. 1.

FIG. 2 is a plan view of a proximal lead connector assembly 50 adapted for use with the stacked subassembly 10 and shell 80 of FIG. 1. Lead connector assembly 50 includes a pin connector terminal 52 and three ring connector terminals 54, 56, and 58. Lead connector assembly 50 may generally correspond to an IS4 connector assembly, having four inline terminals 52, 54, 56 and 58, however, embodiments of the invention may be adapted for use with other lead connector assembly configurations. Each of terminals 52, 54, 56, and 58 are electrically coupled to respective insulated conductors extending through an elongated lead body to electrodes generally positioned along the distal end of the lead body. The terminals 52, 54, 56, and 58 are separated and electrically isolated from one another by insulating structures 60, 62, and 64. Lead connector assembly 50 can be an "in-line" connector assembly or a bifurcated connector assemblies which carry connector terminals on separate branches. In-line lead connector assemblies can have sealing rings along the insulating structures between connector terminals for providing a fluid resistant seal between circuit elements when the lead connector assembly is coupled to an implanted device.

Figure 3:
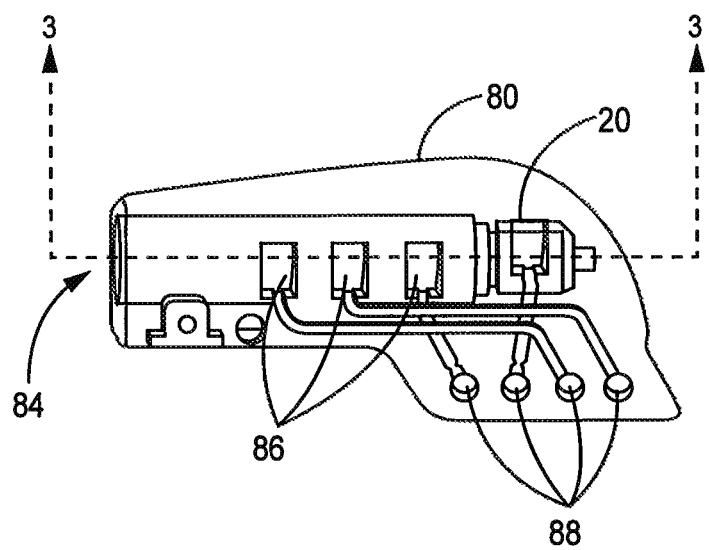
FIG. 3 is an enlarged perspective view of a connector shell including a set of apertures formed therein.
Figure 4:
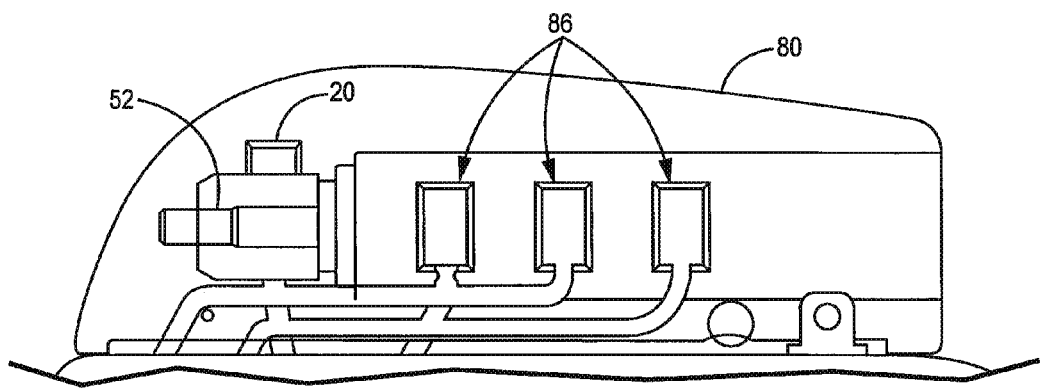
FIG. 4 is a perspective view taken along lines 3-3 of a connector shell including a set of apertures formed therein.
Figure 5:
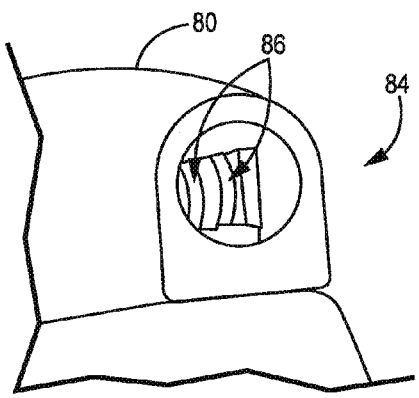
FIGS. 5 and 6 are exploded schematic views of apertures formed down the bore of the shell of FIG. 1.
Figure 6:
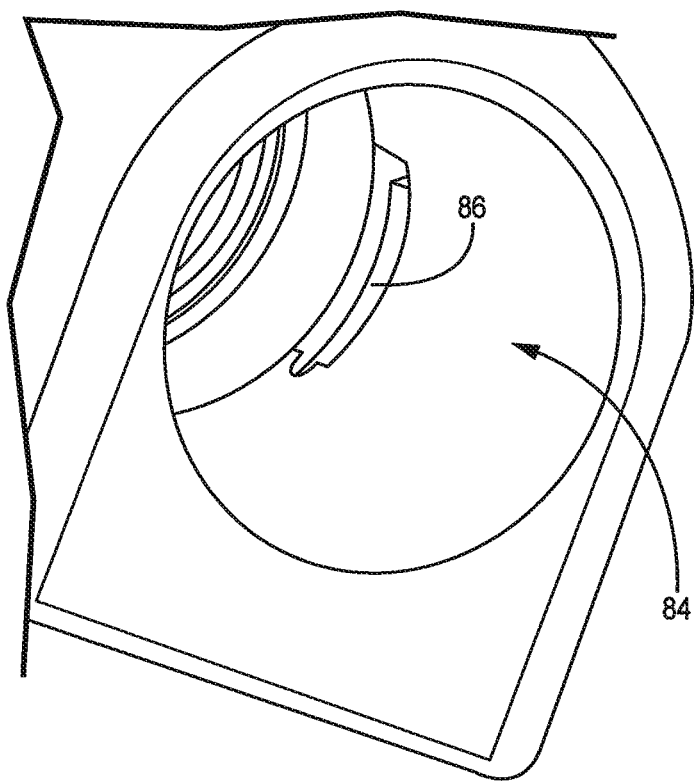
Figure 7A:
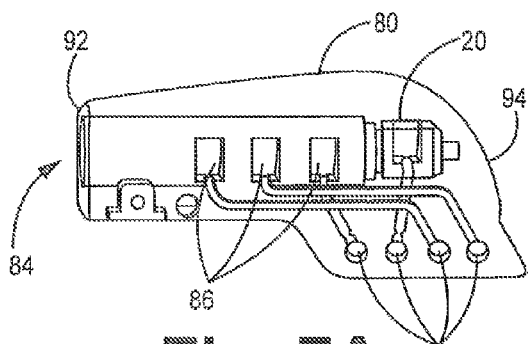
FIGS. 7A-7E are cross-sectional views that depict the operations involved in positioning the stacked assembly into the connector shell and connecting the conductive members in the stacked assembly to a circuit for the implantable medical device.
Figure 7B:
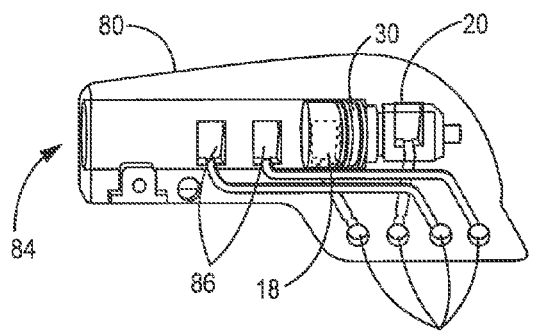
Figure 7D:
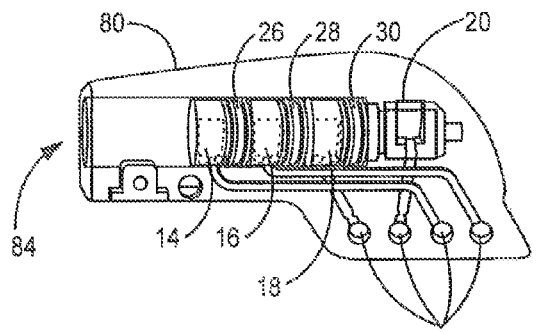
Figure 7C:
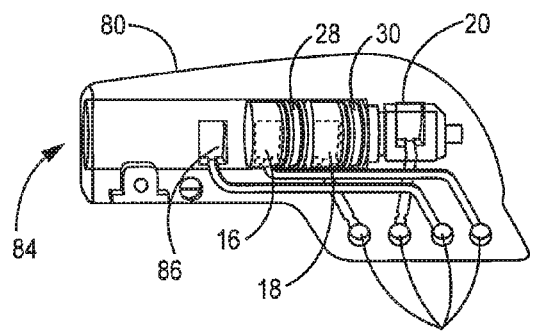
Figure 7E:
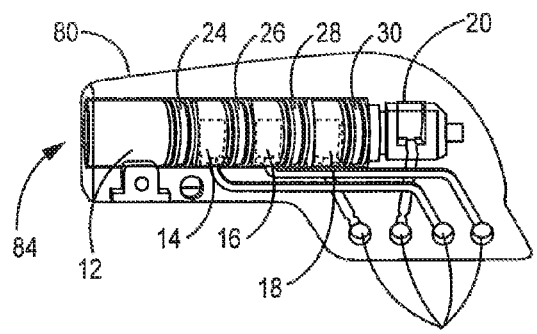

FIG. 3 is a perspective view of shell 80 and FIG. 4 is a top view of a lead connector assembly 50 inserted into a connector assembly shell according to one or more embodiments of the invention. Shell 80 is formed during a single shot casting or molding process. A single shot of molding material means that solely one molding operation and one shot of polymer or mixtures of polymers is used at a single time. An exemplary description of how a molding process is performed is disclosed in U.S. Pat. No. 6,817,905 (Zart et al.), hereby incorporated herein by reference in its entirety; however, one or more embodiments of the present disclosure does not include the overmolding process that is disclosed in Zart. Shell 80 may be formed from a polymer, such as a polyurethane, and may thus be formed during high pressure and/or high temperature processes. Suitable polyurethane materials for forming shell 80 include a 75D polyurethane such as Thermedics™ Tecothane® available from Noveon, Inc., Cleveland, Ohio, or Pellethane™ available from Dow Chemical, Midland, Mich. Thermoset epoxy materials can also be used. Shell 80 is fabricated by loading a mandrel (not shown) in a mold into which the polymer material is applied. Shell 80 is thereby formed having an inner surface 82, which is formed by the mandrel, defining a connector bore 84. Shell 80 may be additionally formed with channels 88, grooves, recesses or other features for receiving, retaining and/or aligning conductive traces of circuit member 90. In one or more embodiments, shell 80 is formed without a permanent metal molded therein. In one or more other embodiments, shell 80 may include embedded components or be formed with other additional features for receiving components during an assembly process, depending on the particular application. For example, the set screw block may be formed in shell 80.

As shown in FIGS. 3 and 4, shell 80 includes connector bore 84, however it is recognized that a connector shell 80 may be formed having multiple connector bore 84 to allow connection of more than one lead to the associated IMD. Shell 80 is formed having a plurality of apertures 86 (i.e. open windows) aligned with traces 92 extending from circuit member (i.e. hybrid board) (not shown). Apertures 86, become filled with conductive connectors 14, 16, and 18 provide access for electrically coupling traces 92 to connectors included in the stacked assembly 10 positioned in connector bore 84. Shell 80 further includes a fill port (not shown) used for delivering an adhesive for creating a bond between shell inner surface 82 and sealing members included in a stacked subassembly inserted in connector bore 84. An over fill port (not shown) is provided to allow excess adhesive and air bubbles to escape during the delivery process.

Figure 12:
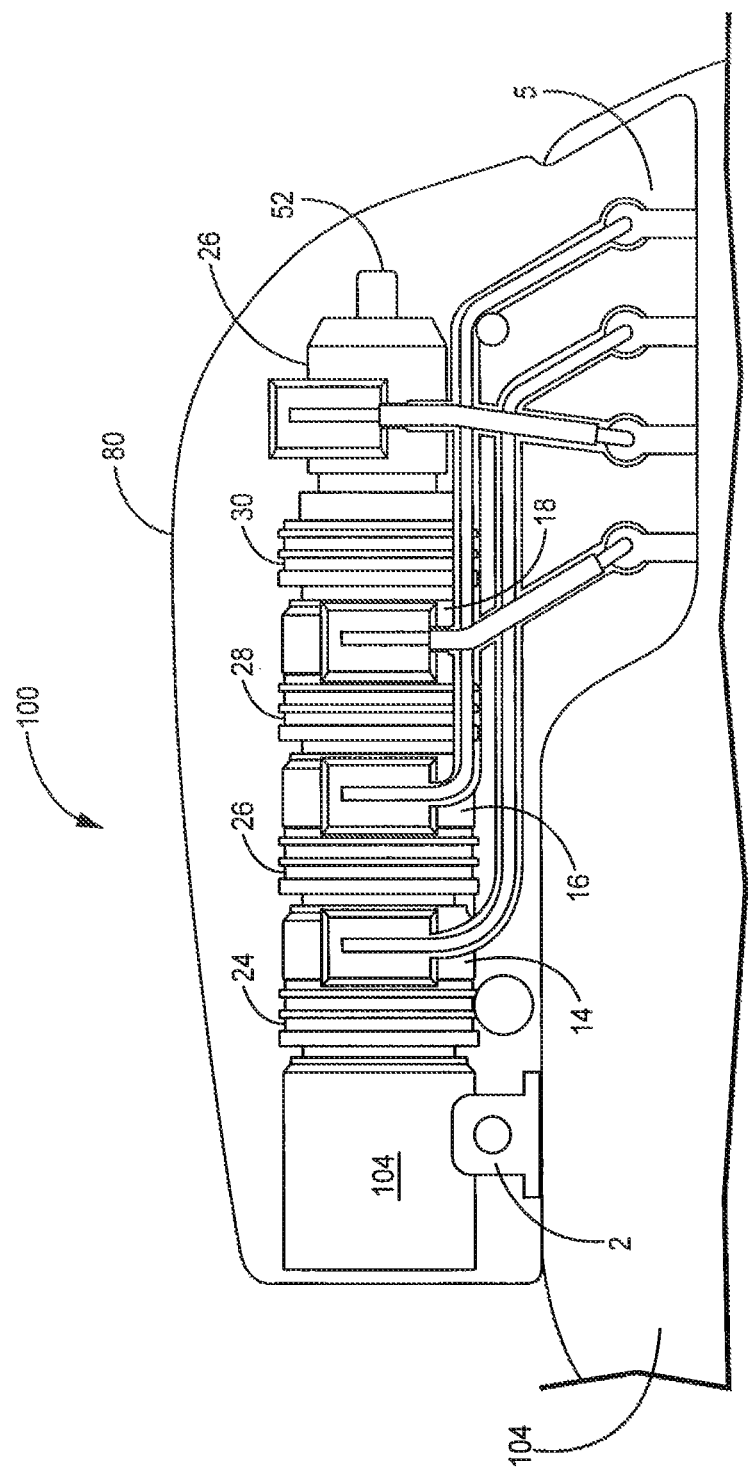
FIG. 12 is a perspective view of a device connector assembly including a molded shell and stacked subassembly inserted into the bore of the molded shell.

Referring to FIGS. 3-6, open windows or apertures 86 are molded into shell 80. The dimensions of each aperture is 1-5 millimeters (mm)×1-5 mm with a depth of 0.5-5 mm. Open windows 86 are configured to receive connectors 14, 16, 18, which allow access for electrically coupling circuit member traces 92 to each of connector members 14, 16, 18. For example, as shown in FIG. 12, traces 92 maybe laser welded to connector members 14, 16, 18 through open windows 86. Windows 86 are subsequently filled with an insulating adhesive, such as silicone rubber to prevent ingress of body fluids around the circuit member connections. Alternatively, a conductive adhesive may be applied through windows 86 in order to electrically couple traces 92 to connector members 14, 16, 18 and set screw block 20. An insulating adhesive may then be applied over the conductive adhesive to seal windows 86.

In still another embodiment, traces 92 and connector members 14, 16, 18 are mechanically coupled to provide electrical connection between the traces and the connector members. For example, traces 92 may be pressed, staked, crimpled, or riveted to connector members 14, 16, 18 and 20 through windows 86. Any suitable method for electrically coupling traces 92 to connector members 14, 16, 18 may be used. Electrical connection of traces 92 with connector members 14, 16, 18 may occur before or after forming adhesive bonds.

Figure 10:
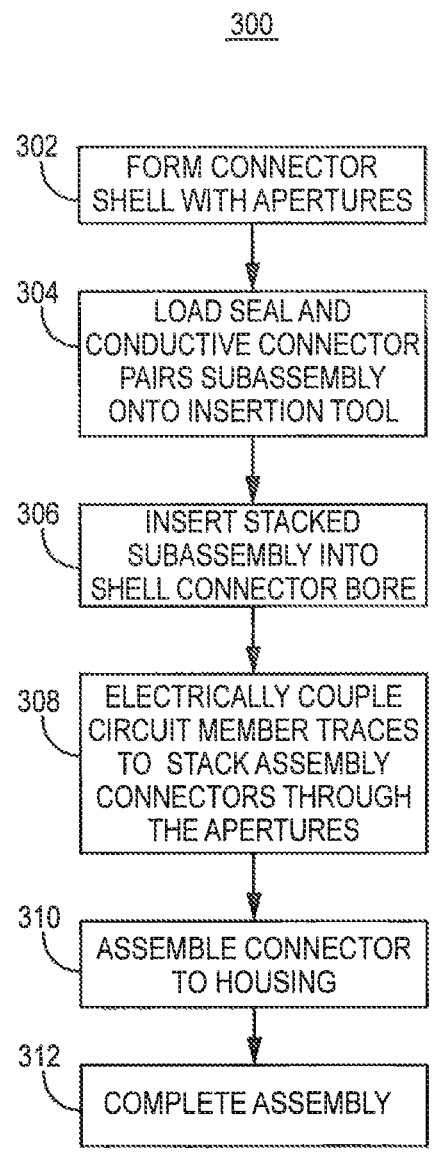
FIG. 10 is a flow chart for a method of inserting a stacked assembly into a connector shell with a set of apertures that allows conductive connectors to be electrically connected with a feedthrough assembly.

The flow chart of FIG. 10 describes the formation of a connector assembly for use in an implantable medical device while FIGS. 7A-7E provide cross-sectional views of connector shell 80 as each operation is performed in order to form the connector assembly. Method 300 includes assembling a mandrel in a mold for forming a connector shell at block 302. Typically, the shell 80 is comprised of one or more polymer materials such as polyurethane in a high temperature, high pressure process. A shell inner surface 82 is formed by the mandrel defining a connector bore 84.

The connector shell 80 is molded at block 304 using a one shot molding process. The one shot molding process employs one or more polymers that is used during a single run of the molding machine. In one or more embodiments, an overmold process is not used. The molded shell, shown in FIG. 7A, includes first and second ends 92, 94 with a bore 84 extending between the first and second ends 92, 94. In one or more embodiments, the plurality of apertures 86 are radially disposed along the bore 84 and extend through the connector shell wall 96. The apertures 86 are spaced apart from each other. Apertures 86 serve the purpose of allowing the conductive lines or traces extending from a feedthough assembly to pass through the apertures 86 to the conductive connector members 14, 16, 18 of a stacked assembly 10.

The shell 80 may further include other features such as a fill port for injecting adhesive for bonding the shell inner surface 82 with the outer surface of sealing members positioned in the connector bore 84, set screw apertures, and other features for accommodating additional connector bore 84 circuit members, connectors, or other components to be included in the connector assembly.

Figure 8A:
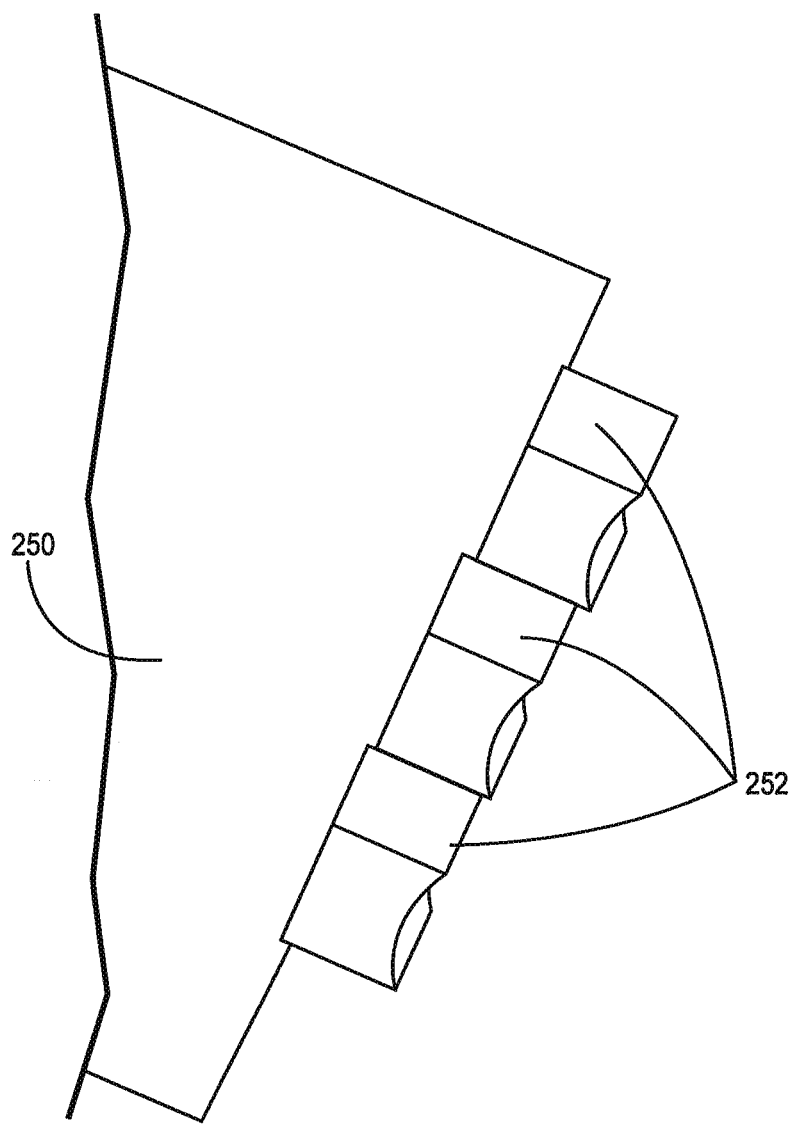

Optionally, a mating tool 250 is used with either the first or second embodiments of shells such that the mating tool 250 is moved over the shell 80 until the mating tool head is adjacent to the plurality of apertures at block 306. The mating tool 250 can be used to plug the apertures 86 to further assist seals to more easily move over or across the open windows 86 without the seals being deleteriously affected. Skilled artisans will appreciate that the mating tool 250 is not required to place or position pairs of sealing and conductive members down the bore 84. An exemplary mating tool 250 is shown in FIGS. 8A-8B. While mating tool 250 is depicted as a body with two rectangular shaped prongs 252 or protruding members extending from the body, skilled artisans understand that a shell connector 80 that includes three apertures 86 requires a mating tool 250 with three prongs to corresponding fit apertures 86 and project to the proper depth to complete the cylindrical surface of the main bore 84.

At block 308, a stacked subassembly is formed along the connector bore 84 by inserting pairs of members down the bore 84 as shown and described relative to FIG. 7. Each pair comprises a first conductive member and a first sealing member. The pair are moved together such that the conductive member has a surface exposed by an aperture or window formed in the shell. After one pair is inserted down the bore 84, another pair is inserted down the bore 84. More specifically, the stacked subassembly is formed by positioning a first pair (FIG. 7B), second pair (FIG. 7C), and third pairs (FIG. 7D), of conductive connector members 14, 16, and 18 interleaved with sealing members 24, 26, 28 along the connector bore 84 such that the conductive member is disposed within an aperture 86. In one or more embodiments, each pair includes a sealing member and a conductive member that interlock together. Each conductive connector member 14, 16, and 18 of each pair is disposed within an aperture 86. End cap 12 is then inserted down the bore 84 as shown in FIG. 7E. A fluid-resistant interface is formed between the outer surface of the sealing members and the inner surface of the connector shell 86 via the compressed state of the sealing member outer diameter against the inner surface 82 of bore 84.

Figure 8C:
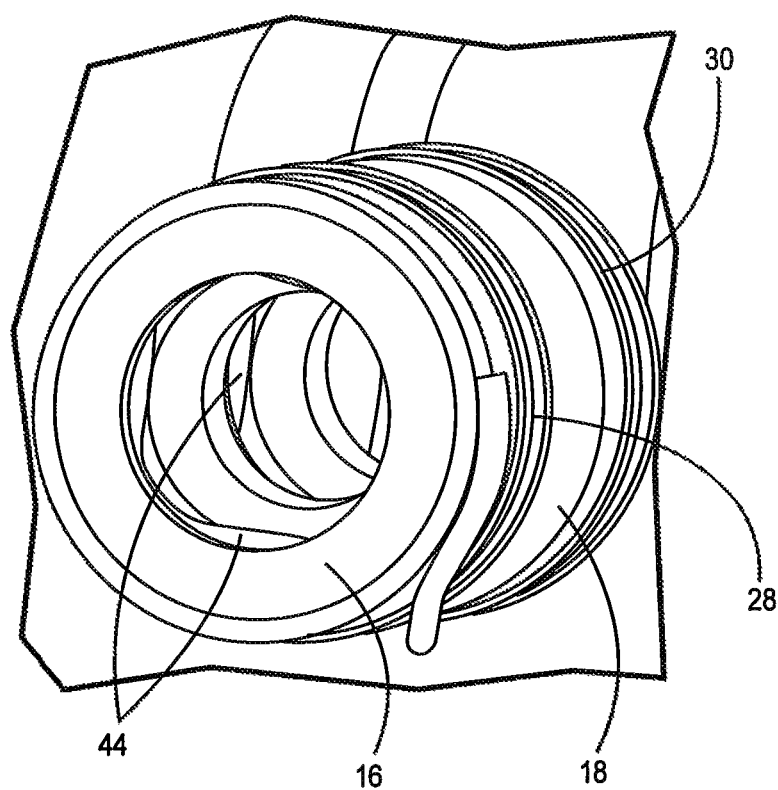
FIG. 8C is an enlarged schematic view down the bore depicting pairs comprised of a seal member and a conductive member with a conductive clip disposed along an inner surface of each conductive member.

FIG. 8C depicts a conductive clip 44 disposed within each of the conductive connector members 14, 16, and 18. Conductive clip can be formed in one or more conductive pieces. An exemplary conductive clip is shown and described in U.S. Pat. No. 8,706,229 issued Apr. 22, 2014, and assigned to the assignee of the present invention, the disclosure of which is incorporated by reference in its entirety herein.

In one or more other embodiments, stacked subassembly 10 is separately formed and then inserted into bore 84. For example, stacked subassembly 10 including sealing members, connectors and an end cap, which may be provided with interlocking features, are loaded onto an insertion tool 254. Using the insertion tool 254, the stacked subassembly is inserted into the shell connector bore 84, as is shown in FIG. 9. Retention members (not shown) may be provided along the stacked subassembly outer diameter for engaging the shell inner surface 82 and securing the stacked subassembly 10 within the connector bore 84 upon full insertion. A second insertion tool may be used to compress the stacked subassembly within the connector bore 84.

After the stacked assembly is down the bore 84, the optional mating tool 250 can then moved away from the plurality of the apertures 86 in response to the plurality of conductive members being positioned along the connector bore 84 such that each conductive member is located within an aperture 86. A plurality of wires 46 (also referred to as conductive traces) extending from a circuit member are coupled to the plurality of conductive members extending through a side of the shell.

The circuit member traces are electrically coupled to stack assembly 10 conductive connector members 14, 16, and 18 through the windows or apertures 86 that leaves a portion of the surface of the conductive connector members 14, 16, and 18 exposed. The exposed surface of the conductive connector member 14, 16, and 18 is electrically connected to the circuit through the traces 92. Electrical coupling between circuit member traces and conductive connector members 14, 16, 18 may involve welding, or application of conductive adhesives. Electrical coupling between traces and connectors may additionally or alternatively include mechanical coupling between the traces and connectors involving riveting, staking, crimping or a protruding mechanical coupling member such as a spring, barb, button, or beam.

Figures 11, 11A:
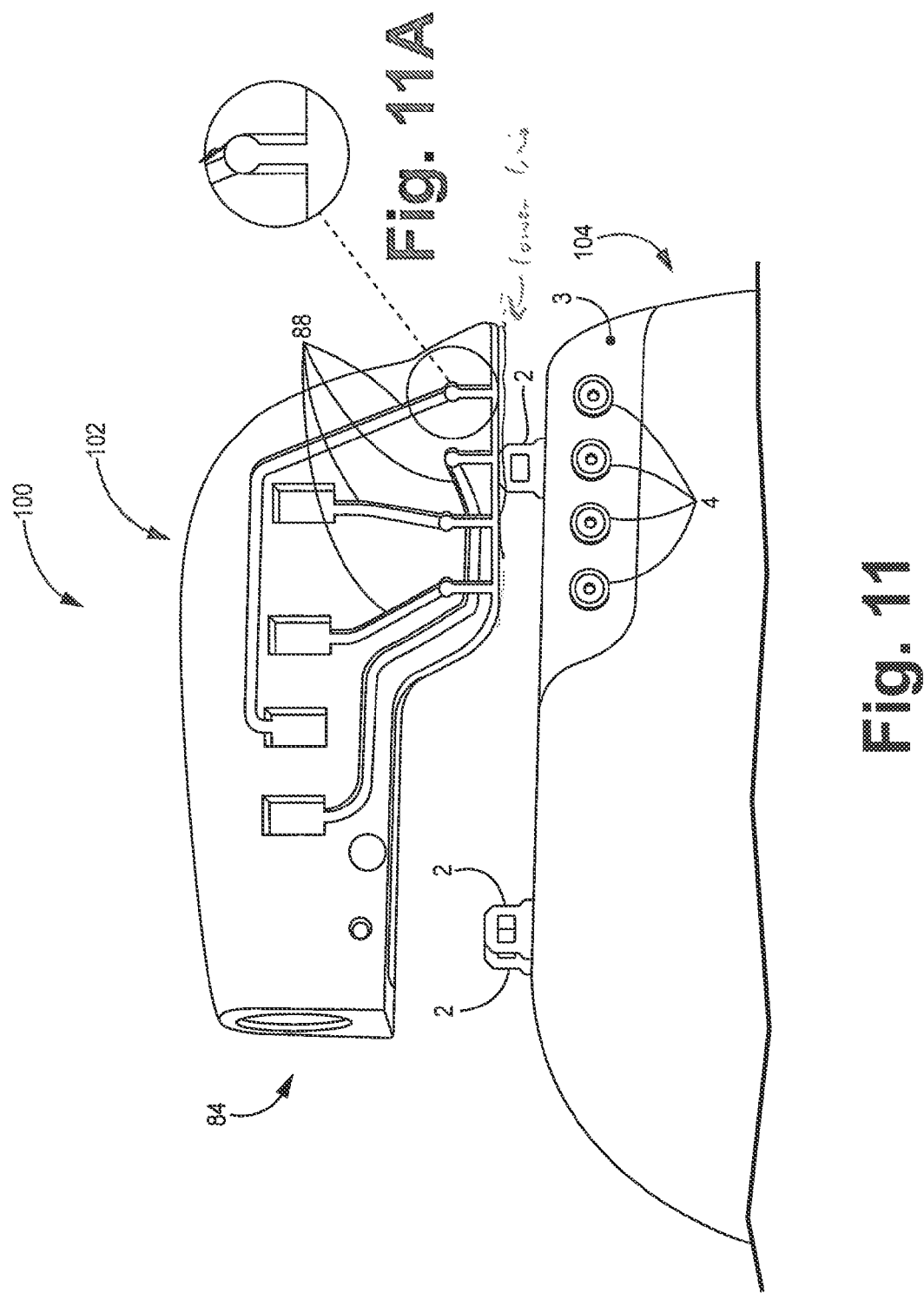
FIG. 11 is a perspective view of a connector assembly positioned over the can prior to the connector assembly being attached with pins to the can.
FIG. 11A is an exemplary key hole slot channel.

The connector assembly 102 is assembled with housing 104 to form implantable medical device (IMD) 100 at block 314, as is shown in FIG. 11. The connector assembly 102 is placed over the housing 104 (also referred to as the device case or can). In particular, the implantable medical device connector assembly 102 is secured to the housing 104.

Wires 46 are connected to cover 48. Cover 48 comprises the same or different conductive material as wire 46. Cover 48 is depicted as rectangular in shape but can be configured as any shape provided that cover 48 covers aperture 86. Wires 46 are routed via grooves 88 and the wire 46 is then welded (e.g. hot welded such as spot welded, cold welded) to wire 44. The connector assembly 102 is pinned in place to the housing 104. Weld tab 2 helps to mechanically hold or secure the connector assembly 102 to the housing 104. The feedthrough wires are either brazed to feedthrough insulators 4 or glassed in. Feedthrough insulators 4 isolate the feedthrough wires electrically from the device case, while also providing a hermetic seal for IMD 100.

FIG. 12 is a cut-away perspective view of a device connector assembly including a molded shell 80 and stacked subassembly 10 formed down the bore 84 of the molded shell 80. As previously described, connector assembly 102 includes molded shell 80 formed during a molding process that includes windows or apertures 86 to allow circuit member traces to directly connect with conductive connector members of the stacked assembly 10. A stacked subassembly 10 is inserted into connector bore 84 having receptacle in end cap 12 for receiving a lead connector assembly. The stack assembly 10 may be inserted in sections (e.g. one or two pairs of seal members and conductive connector members) to better control the position of each contact. In an alternative embodiment, the stack assembly 10 can be pre-assembled and then positioned within bore 84 through a single insertion. Connector assembly 102 may further include one or more additional receptacles for receiving additional leads in one or more additional connector bore 84. Connector assembly 102 includes a set screw aperture for receiving a set screw advanced into a set screw block positioned along connector bore 84. Connector assembly 102 may include additional set screw apertures as needed for receiving additional set screws used for securing lead connector assemblies positioned in other connector bore 84. Connector assemblies may alternatively be fabricated with other connectors in place of set screw blocks, such as spring connectors, for receiving lead connector pins, thereby eliminating the need for set screw apertures.

Figure 13:
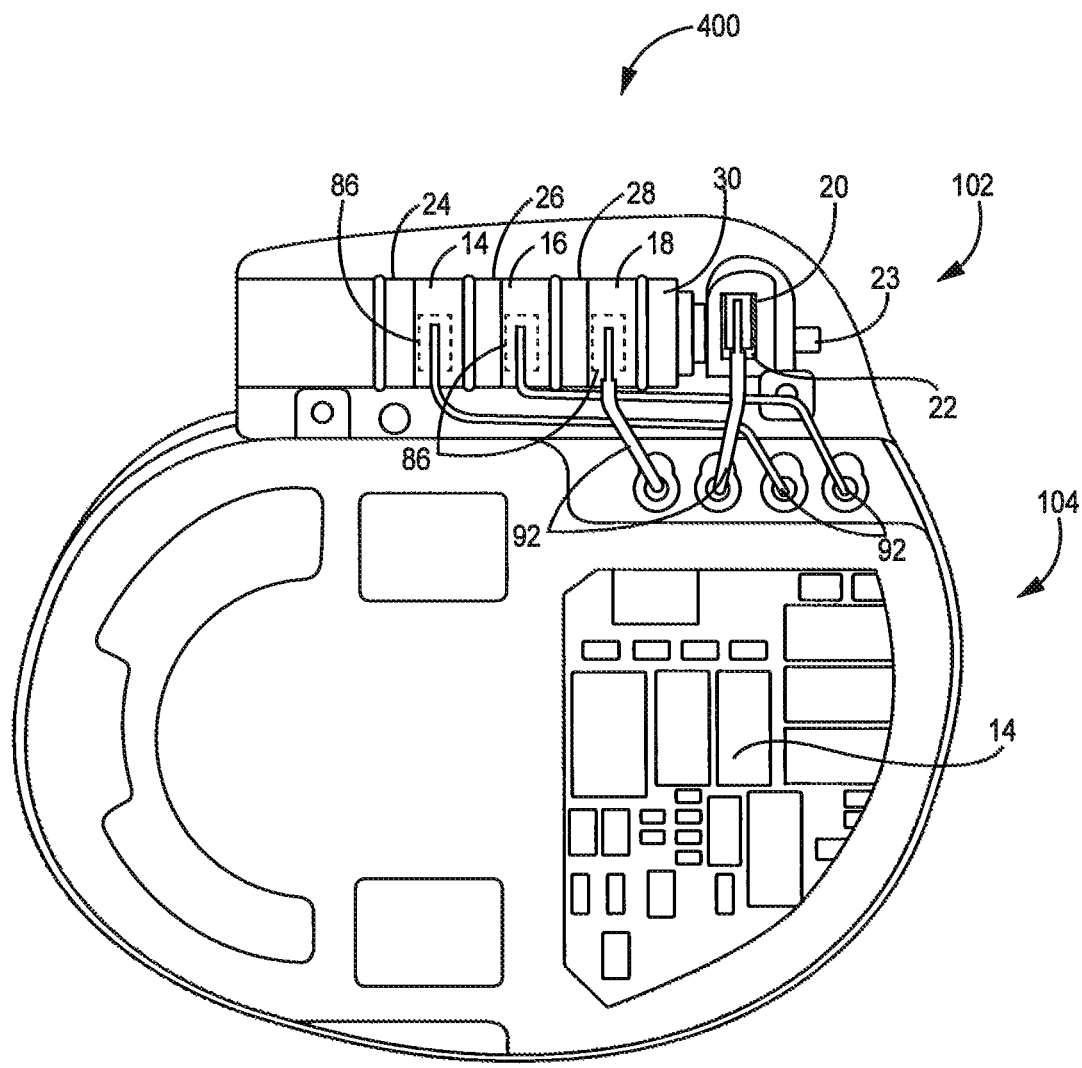
FIG. 13 is a perspective view of the completed connector assembly coupled to an implantable medical device (IMD).

FIG. 13 is a perspective view of the completed connector assembly 102 shown in FIG. 12 coupled to housing 104 to form an IMD 400. IMD 400 may be a pacemaker, cardioverter/defibrillator, neurological stimulator, physiological monitor, or any other implantable medical device utilizing medical leads. In particular, sealing members are provided along a stacked subassembly 10 for creating a fluid-resistant seal with insulating portions of a lead connector assembly inserted into a receptacle. The sealing members also form a fluid-resistant interface with the inner surface of shell 86 along the outer surface of the sealing members. Stacked subassembly 10 is assembled with or without an insertion tool and inserted in connector shell 86 after shell 86 has been molded. The circuit member (also referred to as a hybrid board), partially embedded in connector shell (not shown), may be trimmed and electrically connected to internal circuitry enclosed in IMD housing. Electrical connection between IMD internal circuitry (not shown) and the circuit member is typically made via a feedthrough array extending through hermetically sealed housing.

Figure 14:
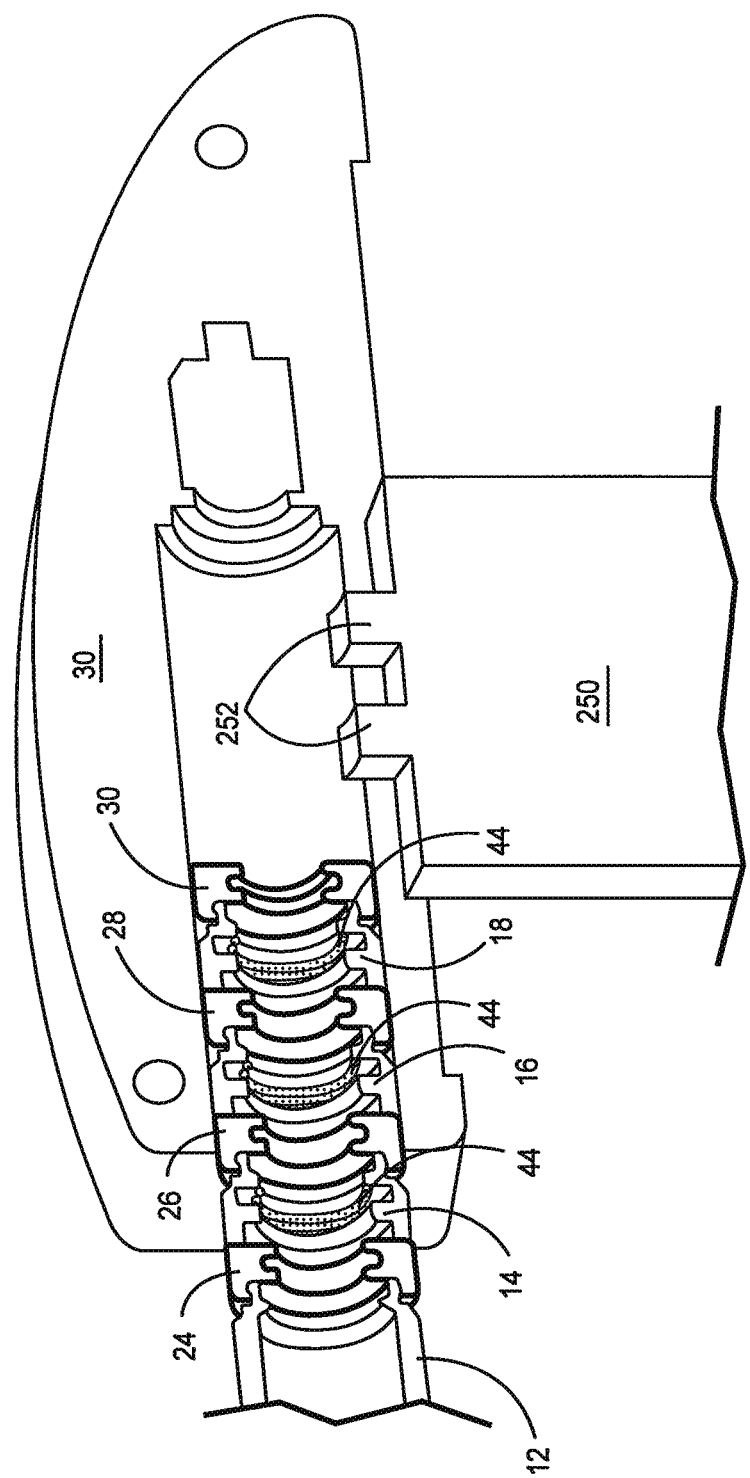
FIG. 14 is a schematic view of a mating tool used to fill apertures in a connector shell so that the inner surface down the bore of the connector shell is substantially flush.

While the present disclosure has been described with molded shell 80 including three apertures 86 or open windows, skilled artisans appreciate that shell 80 could be molded with only two apertures 86. Accordingly, only two pairs of conductive connector members and sealing members would be used in stacked assembly 10. The mating tool would be configured to include two protruding prongs, shown in FIG. 14, to cover apertures 86 in order to allow the pairs to be easily inserted down the bore 84. From this stacked assembly 10, each conductive connector member would fit into a single aperture 86. Thereafter, wire 46 and cover 48 would be connected to wire 44.

Figure 15:
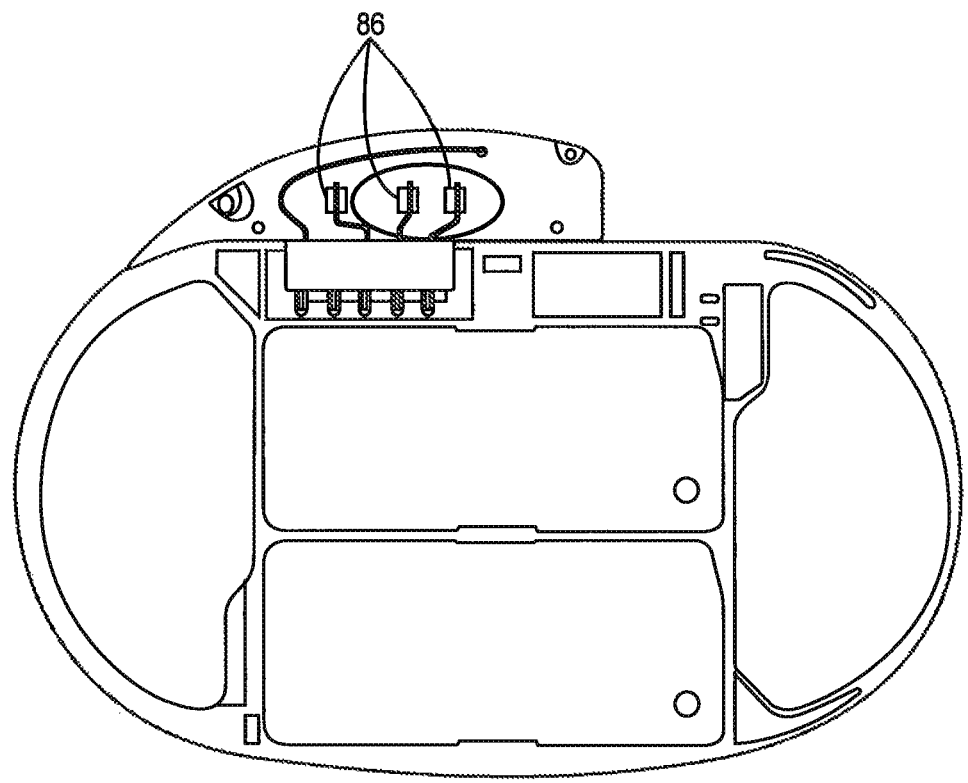
FIG. 15 is a perspective view of yet another completed connector assembly coupled to an IMD.

FIG. 15 is a perspective view of yet another completed connector assembly coupled to the housing 104 to form an IMD. The IMD may be a pacemaker, a cardiac resynchronization therapy pacemaker, a cardioverter/defibrillator, neurological stimulator, physiological monitor, or any other implantable medical device utilizing medical electrical leads. The completed connector assembly can be optionally formed solely using the two prongs extending from the mating tool of FIG. 14 so that the connector bore 84 is flush within the bore 84 while the pairs of connector members and sealing members are slid down the bore 84. Stacked subassembly 10 is assembled with or without an insertion tool and inserted in connector shell 86 after shell 86 has been molded. The circuit member (also referred to as a hybrid board), partially embedded in connector shell (not shown) includes legs that, may be trimmed and electrically connected to internal circuitry enclosed in IMD housing. Trimmed means that the legs are cut-off from the board. Electrical connection between IMD internal circuitry (not shown) and the circuit member is typically made via a feedthrough array extending through hermetically sealed housing.

Thus, an electrical medical device connector assembly incorporating a connector shell including a plurality of apertures (e.g. windows) configured to receive conductive connectors subsequently coupled to the hybrid board of the implantable medical device and an associated fabrication method have been presented in the foregoing description with reference to specific embodiments. It is appreciated that various modifications to the referenced embodiments may be made without departing from the scope of the invention as set forth in the following claims.

The invention claimed is:

1. A method for forming an implantable medical device including a connector assembly adapted for receiving a medical electrical lead, the method comprising:
providing a circuit member comprising electrical circuitry;
molding a shell having first and second ends and defining a bore extending between the first and second ends, the shell further including a plurality of windows disposed along the bore;
moving a mating tool adjacent to the plurality of windows, the mating tool comprising a head having a set of prongs;
positioning the set of prongs within the plurality of windows to close each window while forming a stacked subassembly within the bore, the stacked subassembly comprises:
positioning a first pair of members along the bore, the first pair of members comprises a first sealing member and a first conductive member, the first sealing member positioned at a bore distal end, the first conductive member is positioned adjacent to the first sealing member and a portion of the first conductive member adjacent one of the plurality of windows covered by the set of prongs; and
positioning a second pair of members along the bore, the second pair of members comprises a second sealing member and a second conductive member, the second sealing member positioned adjacent the first conductive member and a portion of the second conductive member adjacent one of the plurality of windows covered by the set of prongs;
removing the set of prongs from the plurality of windows; and
coupling a plurality of conductive traces extending from the circuit member to the plurality of conductive members extending through a side of the shell.

2. The method of claim 1 wherein the set of prongs extending from the mating tool allows the first and second pairs of members to easily move down the bore.

3. The method of claim 1 wherein the mating tool blocks each window of the plurality of windows.

4. The method of claim 1 further comprising inserting an end cap seal assembly into the cylindrical shell to complete a down a bore assembly.

5. The method of claim 1 wherein solely single shot operation is performed to create the connector assembly.

6. The method of claim 1 wherein solely single bore for receiving a medical electrical lead is formed in the connector assembly.

7. The method of claim 1 wherein the mating tool includes a set of prongs configured to fit within corresponding ones of the plurality of windows in the shell.

8. A method for forming an implantable medical device including a connector assembly adapted for receiving a medical electrical lead, the method comprising:
providing a circuit member comprising electrical circuitry;
molding a shell having first and second ends and sides extending therebetween and first and having a bore extending between the first and second ends, the shell further including a plurality of windows disposed along the bore and each extending through a side of the shell;
moving a mating tool adjacent to the plurality of windows, the mating tool comprising a head having a set of prongs;
positioning the set of prongs within the plurality of windows to close each window while providing a stacked subassembly within the bore, wherein placing the stacked subassembly comprises:
positioning first and second pairs of members along the bore, the first pair of members comprising a first sealing member and a first conductive member, the second pair of members comprises a second sealing member and a second conductive member, the first sealing member being positioned at a bore distal end, the first conductive member being positioned adjacent to the first sealing member and a portion of the first conductive member adjacent a first one of the plurality of windows covered by the set of prongs, the second sealing member being positioned adjacent the first conductive member and a portion of the second conductive member being positioned adjacent a second one of the plurality of windows covered by the set of prongs;

removing the set of prongs from the plurality of windows; and coupling a plurality of conductive traces extending from the circuit member and through the plurality of windows to the plurality of conductive members.

9. A method according to claim 8 wherein providing the first and second pairs of members along the bore comprises placing the first and second pairs of members on an insertion tool and inserting the pairs of members into the bore using the tool.

* * * * *